(12) United States Patent
Herzog

(10) Patent No.: US 6,241,668 B1
(45) Date of Patent: Jun. 5, 2001

(54) MEDICAL SYSTEM ARCHITECTURE

(75) Inventor: Norbert Herzog, Nuremberg (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/231,291

(22) Filed: Jan. 15, 1999

(30) Foreign Application Priority Data

Jan. 23, 1998 (DE) .............................................. 198 02 572

(51) Int. Cl.$^7$ ...................................................... A61B 5/05
(52) U.S. Cl. ............................................................ 600/407
(58) Field of Search ....................... 600/407; 250/363.01; 395/230, 235, 248; 364/40; 705/1, 2, 3, 4, 5, 30

(56) References Cited

U.S. PATENT DOCUMENTS

| | | |
|---|---|---|
| 5,241,466 | 8/1993 | Perry et al. . |
| 5,920,317 * | 7/1999 | McDonald ............................ 345/356 |
| 6,003,007 * | 12/1999 | DiRienzo .................................. 705/4 |
| 6,034,605 * | 3/2000 | March ................................. 340/573.1 |
| 6,076,066 * | 6/2000 | DiRienzo et al. ......................... 705/4 |

FOREIGN PATENT DOCUMENTS 2288511    10/1995 (GB) .

OTHER PUBLICATIONS

"Bilgebende Systeme für die medizinische Diagnostik," Morneburg, 3rd Edition, 1995, pp. 680–696.

* cited by examiner

Primary Examiner—Teresa Walberg
Assistant Examiner—Daniel Robinson
(74) Attorney, Agent, or Firm—Schiff Hardin & Waite

(57) ABSTRACT

A medical system architecture include at least one modality for acquiring medical images, an apparatus for processing the medical images and for accepting patient-related data, an apparatus for communicating the images and data, and an apparatus for storing the images and patient-related data. Furthermore, an apparatus for the digital acquisition of optical images, such as a photo camera, a video camera and/or a scanner, is connected to the apparatus for communication, it being possible to store the digitized optical images in the apparatus together with the medical images and patient-related data.

6 Claims, 2 Drawing Sheets

MEDICAL SYSTEM ARCHITECTURE

BACKGROUND OF THE INVENTION

1. Field of the Invention

The present invention relates to a medical system architecture with a modality for capturing medical images, an apparatus for processing the medical images and accepting patient-related data, an apparatus for transmitting the images and data, and an apparatus for storing the images and the patient-related data.

2. Description of the Prior Art

The book Bildgebende Systeme für die medizinische Diagnostik; H. Morneburg, $3^{rd}$ Edition, 1195: 680ff teaches medical system architectures in which, for the retrieval of patient data and of images created by modalities, image observation and processing locations, known as work stations, are connected to an image communication network. In previous medical imaging systems, medical digital images have been created, processed and archived by means of electromagnetic waves in the invisible region, such as X-ray images, ultrasound images, etc . . . Such conventional medical system architectures with such work stations do not allow a clear identification and allocation of the examined patient to the patient files.

Heretofore, clear, machine-readable patient identifiers have employed a name and/or ID number, for example, which have been added to the digital image data files in a portion thereof known as a header. An unmistakable identification of the patient, however, still is not achieved by such conventional headers.

Furthermore, in many medical cases such as in endoscopy, surgery, and for skin diseases, photographic images are advantageous for the diagnosis and the history of the disease, it being possible to visibly document success of a treatment by means of such photographic images.

British Specification 2 288 511 describes a diagnostic apparatus in which the signal from a video camera is digitized, processed and, after being compressed for remote diagnosis, the compressed data are transmitted over a telephone network.

U.S. Pat. No. 5,241,466 describes a system for managing and storing important documents which are acquired by an optical scanner and are stored on a CD ROM.

SUMMARY OF THE INVENTION

An object of the present invention is to provide a medical system architecture of the above type with an electronic patient file from which the patient to whom it pertains is unambiguously discernable and wherein the file enables a documentation of treatment successes in all medical fields.

The object is inventively achieved in a medical system architecture wherein an apparatus for the digital generation or acquisition of photographic images of a patient is connected to the apparatus for communication therewith, it being possible to store such photographic images in the apparatus together with the medical images and patient-related data.

A clear identification of the patient to which the digital personal and image data belong is achieved by this integration of digital photography into systems for the creation, processing and archiving of digital medical images. Furthermore, the patient image file can be expanded by non-medical images such as images before and after an operation.

The apparatus can inventively employ a digital photo camera, a video camera or a scanner.

A forwarding of the images to the family doctor, for example, who is not networked, can be achieved in an embodiment wherein a CD writer for producing CDs on which the digital photographic images can be stored is attached to the diagnostic station.

A global access can be achieved in an embodiment wherein the apparatus for transmitting the images and data is connected to the Internet via a network interface.

DESCRIPTION OF THE PREFERRED EMBODIMENTS

Figure 1:
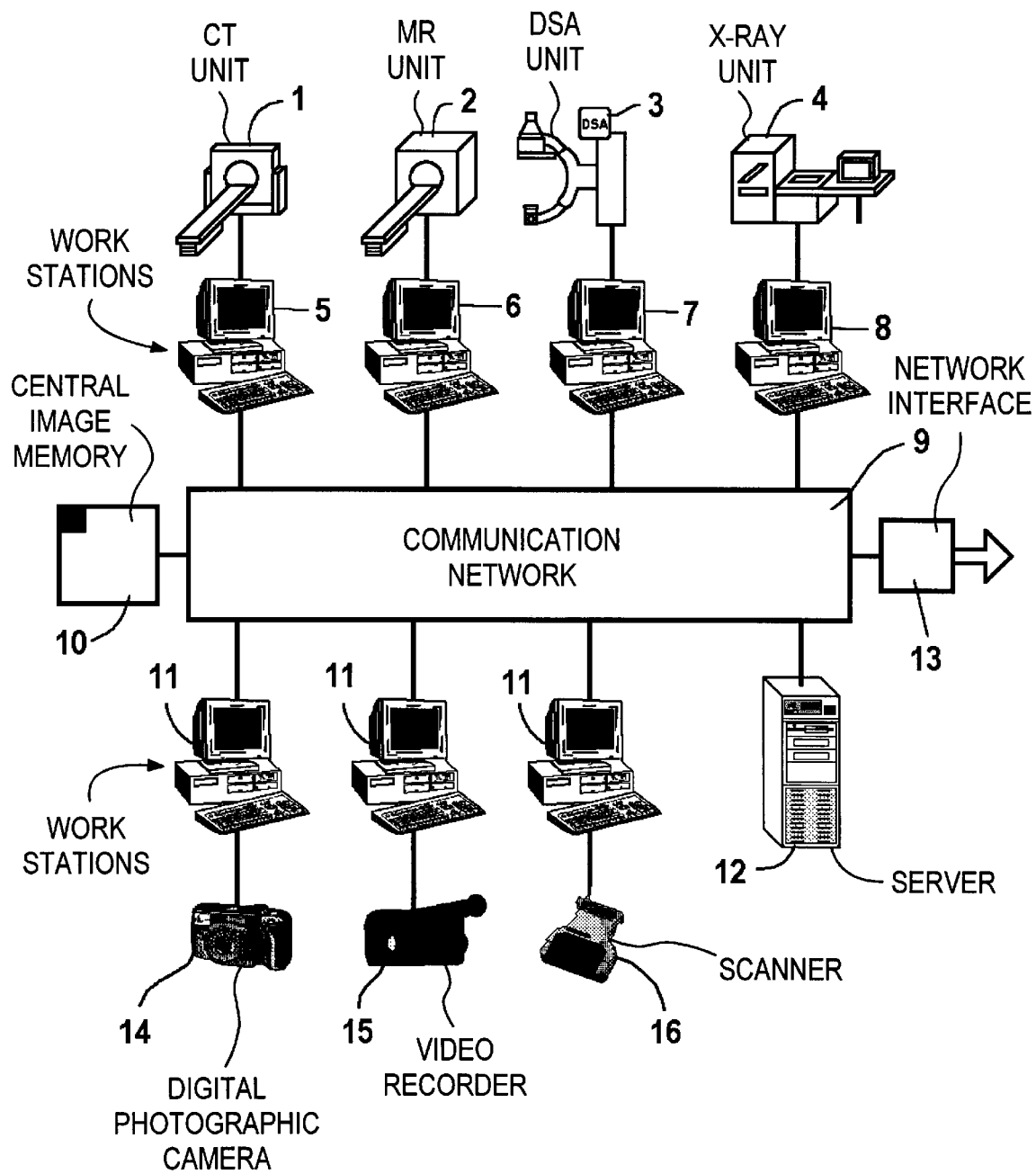
FIG. 1 illustrates a known medical system architecture in which the inventive apparatus can be employed.

FIG. 1 depicts an example of a known system architecture of a medical image communication network. The modalities 1 to 4 serve for the acquisition of medical images; these modalities may be imaging systems such as a CT unit 1 for computed tomography, an MR unit 2 for magnetic resonance imaging, a DSA unit 3 for digital subtraction angiography, and an X-ray unit 4 for digital radiography. Work stations 5 to 8 can be attached to these modalities 1 to 4, it being possible to process and to locally store the acquired medical images therewith. Patient data belonging to the images can also be entered. One such work station is a very fast small-sized computer constructed and operating on the basis of one or more fast processors, for example.

The work stations 5 to 8 are connected to an image communication network 9 for the communication and distribution of the created images. The images produced in the modalities 1 to 4 and the images processed in the work stations 5 to 8 thus can be stored in a central image storage and image archiving system 10 or can be forwarded to other work stations.

Additional work stations 11 are connected to the image communication network 9 as diagnostic consoles, which contain local image memories. In each work station 11, the images which are acquired and filed in the image storage system 10 can be subsequently retrieved for diagnosis and filed in the local image memory, from which they can be made directly available to the diagnostician working at the work station 11.

Furthermore, servers 12—e.g. patient data servers (PDS), file servers and/or program servers, are connected to the image communication network 9.

The image and data exchange via the image communication network 9 can occur according to the DICOM standard, an industry standard for the communication of images and other medical information between computers for enabling digital communication between diagnostic and therapeutic devices of different manufacturers. A network interface 13 can be connected to the image communication network 9, the internal image communication network 9 being connected to a global data network via the interface 13, so that the standardized data can be exchanged among different networks worldwide.

The image communication network 9 also can be connected to the data network of the hospital information system so that additional patient data also can be retrieved.

An apparatus for digital acquisition of optical images, which can be a digital photo camera 14, a video camera 15 and/or a scanner 16, is connected at a work station 11. These apparatuses 14 to 16 also can be connected to the work stations 5 to 8 of the modalities 1 to 4, however. The digital photo camera 14 can be connected directly to the data input of the work station. If an analog video camera 15 is utilized, for example, then an analog/digital converter must be intermediately connected. Electronics can also be connected to the scanner 16 upstream.

Figure 2:
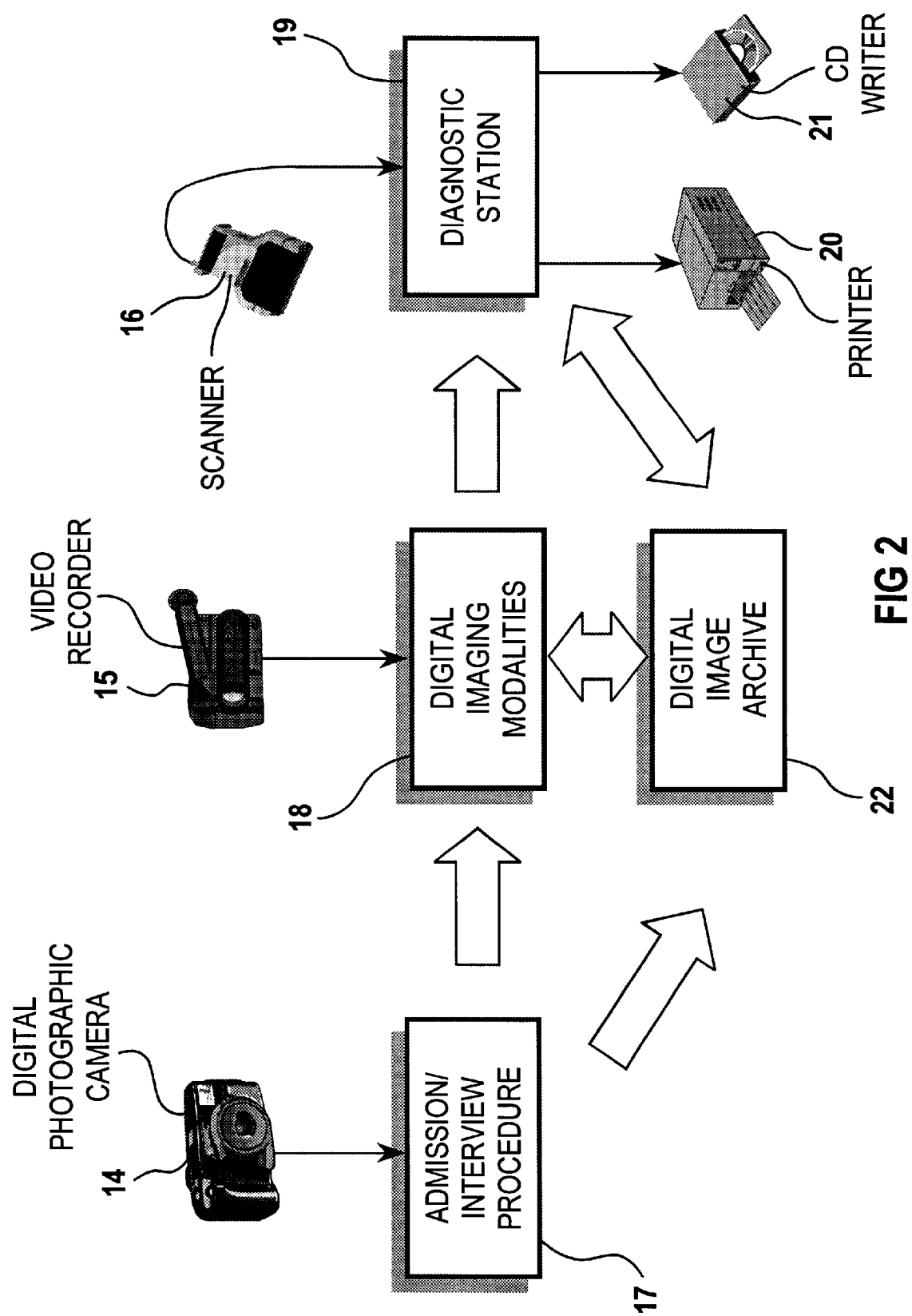
FIG. 2 illustrates the inventive integration of digital photography into digital medical image creation, image processing, and image archiving systems.

FIG. 2 shows details of the inventive integration of digital photography into digital medical image production, image processing, and image archiving systems.

In the patient admission procedure or in an initial examination 17, a pass photo for identification of the patient can be generated by the digital photo camera 14, and medically relevant optical images can be generated. These photographic images can be archived as the first part of a patient image file in a digital image archive 22, such as in the central image memory 10. If relevant to the examination, they also can be transmitted to digital imaging modalities 18 via the image communication network 9. These imaging modalities 18 can be the CT unit 1, the MR unit 2, the DSA unit 3, or the X-ray unit 4.

In turn, medically relevant optical images can be acquired by means of the video camera 15 connected to these modalities 18, for example. These optical images can be forwarded via the image communication network 9 to a digital diagnostic station 19, together with the medical images of the modalities 18, for diagnosis. The optical images also can be stored in the file of the medical images in the digital image archive 22 and only later retrieved, observed and processed by the digital diagnostic station 19.

Additional documents, reports, graphics and/or films relevant to the diagnosis can be scanned in with the diagnostic station 19 via a scanner 16, for example. The scanning masters can be paper printouts in miniature format, such as ultrasound images from the family doctor. The images and data acquired and stored previously or sent by the modalities 18 also can be observed and modified via the image communication network 9.

The digital optical images can be printed out by a printer 20 which is connected to the digital diagnostic station 19. The digital optical images also can be laser recorded on photo CDs by means of a CD writer 21, which is likewise connected to the digital diagnostic station 19, so that they also can be observed by the family doctor, who is not connected to the image communication network 9, or does not have access, at a diagnostic station in his or her practice, for example.

In cases of uncertainty, the correct allocation of the images to the patient can be performed with the aid of a pass image which is created by the digital photo camera 14 and is compulsorily allocated to every patient image file, the pass image being generated in the hospital admission procedure, for example, so that it is clearly recognizable which patient is being examined, even if the patient has a common surname.

In many medical cases, storage of the visible images produced by the video camera 15, for example, is advantageous for the diagnosis and the disease history. The patient image file thus can be expanded by medical modality images which could not be included previously, such as those from a stomach reflection or heart catheter exam. This enables the comparison of endoscopically generated images, images before and after an operation, skin rashes at each time of treatment i.e. even at the beginning of and subsequent to the treatment, so that the treatment progress and the result can be seen clearly. In plastic surgery, body parts which are visible only in the operation can be documented.

The digital optical images are archived in and retrieved from the digital image archive 22 with an identical structure as in the patient image file.

The inventive construction of a medical system architecture with examination methods which are common in medical technology and which utilize digital exposures in the invisible spectral regions enables the acquisition, storage, and retrieval of photographs in the visible spectral region with the digital exposure apparatus as well, so that an advantageous integration of digital photography into digital medical image creation, image processing, and image archiving systems occurs.

The utilization of components for digital photography such as cameras, scanners and printers, for example, enables an inexpensive realization of the inventive construction of a medical system architecture. These components are common and offer standardized JPEG software interfaces, for example. The images thusly acquired can be made available over the Internet. The storage of the image data on photo CDs enables a data exchange in the entire PC world.

Although modifications and changes may be suggested by those skilled in the art, it is the intention of the inventor to embody within the patent warranted hereon all changes and modifications as reasonably and properly come within the scope of his contribution to the art.

I claim as my invention:

1. A medical system architecture comprising:
   at least one modality for producing a medical image of an examination subject;
   a work station for processing said medical image and for entering patient-related data for permanent association with said medical image;
   a communication system connected to said work station for communicating said medical image and said patient-related data to a location remote from said work station;
   a central storage unit connected to said communication system for storing said medical image and said patient-related data; and
   an optical image generating unit for generating digital data comprising a photographic image showing an external appearance of said examination subject, and including means for entering said digital data into said work station for permanent association in said patient-related data with said medical image for unambiguously identifying said examination subject.

2. A medical system architecture as claimed in claim 1 wherein said optical image generating unit comprises a digital photographic camera.

3. A medical system architecture as claimed in claim 1 wherein said optical image generating unit comprises a video camera.

4. A medical system architecture as claimed in claim 1 wherein said optical image generating unit comprises a scanner.

5. A medical system architecture as claimed in claim 1 further comprising a CD writer connected to said work station for digitally recording said photographic image on a CD.

6. A medical system architecture as claimed in claim 1 further comprising a network interface connecting said communication system to the Internet.

* * * * *